United States Patent
Schöpflin

(10) Patent No.: US 10,534,947 B2
(45) Date of Patent: Jan. 14, 2020

(54) DETECTION APPARATUS AND METHOD FOR DETECTING AN OBJECT USING A PLURALITY OF OPTOELECTRONIC SENSORS

(71) Applicant: SICK AG, Waldkirch (DE)

(72) Inventor: Uwe Schöpflin, Waldkirch (DE)

(73) Assignee: SICK AG, Waldkirch (DE)

( * ) Notice: Subject to any disclaimer, the term of this patent is extended or adjusted under 35 U.S.C. 154(b) by 34 days.

(21) Appl. No.: 15/794,238

(22) Filed: Oct. 26, 2017

(65) Prior Publication Data
US 2018/0144168 A1 May 24, 2018

(30) Foreign Application Priority Data
Nov. 24, 2016 (DE) .................. 10 2016 122 711

(51) Int. Cl.
| | |
|---|---|
| G06K 7/14 | (2006.01) |
| G01B 11/25 | (2006.01) |
| G01N 21/84 | (2006.01) |
| G06K 7/10 | (2006.01) |

(52) U.S. Cl.
CPC ........ *G06K 7/1413* (2013.01); *G01B 11/2518* (2013.01); *G01N 21/84* (2013.01); *G06K 7/10722* (2013.01); *G01N 2021/845* (2013.01)

(58) Field of Classification Search
CPC ............. G06K 7/1413; G06K 7/10435; G06K 7/10722; G06K 7/1439
USPC ............. 235/462.11, 462.41, 462.12, 462.14
See application file for complete search history.

(56) References Cited

U.S. PATENT DOCUMENTS

2008/0245873 A1* 10/2008 Dwinell ................. G06T 7/60
235/462.41

FOREIGN PATENT DOCUMENTS

| EP | 2003599 A1 | 12/2008 |
| EP | 2693364 A1 | 2/2014 |

* cited by examiner

*Primary Examiner* — Paultep Savusdiphol
(74) *Attorney, Agent, or Firm* — Nath, Goldberg & Meyer; Jerald L. Meyer

(57) ABSTRACT

A detection apparatus (10) is provided having a plurality of optoelectronic sensors (20) that are arranged in different positions and orientations to record respective image information of different sides of an object (14) and having an evaluation unit (22) to process the image information. In this respect, the evaluation unit (22) is configured to recognize views of a respective side of the object (14) in the image information and to arrange the views in a plane such that the original arrangement on the object (14) can be restored.

14 Claims, 2 Drawing Sheets

DETECTION APPARATUS AND METHOD FOR DETECTING AN OBJECT USING A PLURALITY OF OPTOELECTRONIC SENSORS

FIELD

The invention relates to a detection apparatus having a plurality of optoelectronic sensors and an evaluation unit to process the image information, as well as to a method for detecting objects in which a plurality of optoelectronic sensors record respective image information of different sides of an object in different positions and orientations and the image information is evaluated.

BACKGROUND

To detect an object from all sides using optoelectronic sensors and in particular cameras, multi-systems are used that detect the object from different positions and perspectives. If the detection zone of the camera is not sufficient to completely detect the side for which it is responsible, this can be compensated by a relative movement. The object is typically led past the detection system on a conveyor belt for this purpose. A camera line is then also sufficient that stands at an angle to the conveying direction and that assembles image lines detected after one another to form a total view.

Such a system of conveyor belt and a plurality of cameras is also called a camera tunnel. The detection zone is typically protected from environmental light by a mechanical screening. Such camera tunnels can be used for the inspection or measurement of objects. Image processing methods corresponding to the use adjoin the detection. An important area of use is the reading of codes. In this respect, camera-based code readers are increasingly taking over from the earlier barcode scanners. Code regions are identified in the camera images and are then decoded. Camera-based code readers also cope without problem with different code types than one-dimensional barcodes which also have a two-dimensional structure like a matrix code and provide more information. Automatic text recognition (OCR) is also conceivable. Corresponding reading tunnels are used, for example, in the automatic storing and associating of packages, in flight baggage handling or in logistics centers.

In order now to be able to recognize the objects from all sides in a camera tunnel or to be able to read codes everywhere in the case of a reading tunnel, that is to carry out a so-called omnidirectional reading, six cameras are, for example, provided that detect the object from the top and bottom and from both sides obliquely from the front and obliquely from behind. Each camera takes an image of the object, either in one shot or successively by assembling image lines. The images of the lateral cameras also comprise two sides of an object depending on the rotational position of the object. The camera tunnel consequently outputs six images that each show one or more sides of the object. The images are then transmitted over a network, for example. This is, however, relatively complex because a plurality of images for the same object are transferred and evaluated whose information is redundant in part and where the association of an image section to the original location on the object is difficult to access.

An optoelectronic sensor for detecting codes that sectionally reads images of objects moved on a conveyor is known from EP 2 003 599 A1. A first aspect of EP 2 003 599 A1 is the binarization of the detected gray image data or color image data in real time still during the reading in of further sections. Another aspect deals with combining and outputting the information such as raw image data, code regions or results of a decoding in a structured file. Dealing with a plurality of sensors and their different perspectives is, however, not facilitated in this manner.

SUMMARY

It is therefore the object of the invention to provide improved image information with a detection device of the category.

This object is satisfied by a detection apparatus having a plurality of optoelectronic sensors and by a method for detecting objects in accordance with the respective independent claim. At least two optoelectronic sensors are provided in the detection apparatus that observe a detection zone from different perspectives. Different sides of the object can thereby be recorded, with this in no way precluding a partial overlap. The invention now starts from the basic idea of consolidating the image information so that the sides of the object remain recognizable on the object in their original arrangement, and indeed preferably without doubling. One respective view toward each relevant side is preferably extracted from the image information for this purpose and these views are then suitably arranged in a plane such that the proximity relationships of the sides on the three-dimensional object also remain recognizable in a flat image. Relevant side in this respect means that the detection apparatus is not necessarily intended for all the sides and should not or cannot detect the ground or another side of an object.

The invention has the advantage that the detection apparatus can provide image data that can be evaluated much more simply in an intuitive manner and in an image evaluation process. For, on the one hand, the views can be restricted to the relevant sections of the object sides, with redundancy being avoided. In addition, the original object geometry remains recognizable by the suitable arrangement in one plane such that image information can immediately be spatially associated.

The optoelectronic sensors are preferably cameras that can be configured as matrix cameras, but also as line cameras, with then image lines being detected successively and being assembled to form one record of the object from the respective perspective. In principle, a laser scanner can also deliver image data by evaluating the remission. Hybrid forms with different types of optoelectronic sensors for image detection are technically possible, but not customary. In a particularly preferred further development, they are code-reading sensors, that is camera-based code readers or barcode scanners. The functionality for decoding can, however, equally be implemented centrally, for example in an evaluation unit of the detection apparatus or completely downstream, instead of decentrally in the individual sensors.

The evaluation unit is preferably configured to arrange the views in a folded shape. A folded shape means that the views could be cut out together and can be folded together again to form the three-dimensional object. The folded shape is also called a net geometrically. Particularly with automatic sorting applications, the objects are very frequently at least roughly cuboid in shape so that a net of a cuboid is preferably produced. If the approximation to the cuboid shape of the object is not correct, this will result in aberrations, but by no means means that the net cannot be further evaluated. The object therefore by no way has to be an exact cuboid; shears as with a parallelepiped or certain curvatures of the sides of the object are by all means admissible. It is also conceivable to adapt the net to a known or expected geometry differing from a cuboid.

The detection apparatus preferably has a geometry detection sensor that is configured for the detection of the geometry of the objects using distance data and/or the remission behavior of the objects. It can, for example, be a laser scanner that is arranged upstream of the optoelectronic sensors against the conveying direction. The views and the sides of the object can be made more specific with the help of the then known geometry and a suitable net can be selected, for example. The geometry detection sensor can also be integrated in one or more optoelectronic sensors, for example by a time of light process (such as PMD, photonic mixing detection) or by a stereoscopic evaluation.

The sensors are preferably arranged for an omnidirectional reading from all sides. Not only the correct arrangement, but also the correct number of sensors are required for this purpose. An exemplary possibility is the arrangement of a respective one sensor at the top, bottom, right, left, front and back. The four lateral sensors can be arranged offset, as described in the introduction, and then record two respective sides of the object obliquely from the front and obliquely from the rear. The term omnidirectional reading is also used in a slightly blurred manner when not all the sides are actually detected, for example not the floor. An inspection window would be required for this purpose that is not always available.

The evaluation unit is preferably configured to cut out a respective view from the image data. The sensors typically record a larger portion than only one side. The further image data can include background or, for instance in the case of a sensor directly obliquely onto the object, parts of at least one further side of the object. A corresponding region is therefore cut out (cropping) to obtain only one view of each relevant side. If a side of an object has been detected multiple times, one of the shots can be selected or a higher quality view can be produced from the redundant image data.

The evaluation unit is preferably configured to adapt the views to one another, in particular by rotation and/or rescaling. Views can be brought into a predefined orientation by rotation. A rescaling provides that all the views have the same scale, for example the same number of pixels at common edges.

The evaluation unit is preferably configured to combine the views in the arrangement in a plane to form one image. A common image is thus produced having exactly one respective view of each relevant side of the object. Only a single image consequently has to be forwarded and/or evaluated.

The evaluation unit is preferably configured to output views with information on their arrangement with respect to one another. A piece of meta information is thus available, for example where an expected view is located in an output common image, in addition to the views. Conversely, the views can also be output individually, together with meta information on how they would have to be positioned with respect to one another in a common image.

The evaluation unit is preferably configured to output a structured description or file with views and information on its identity and/or arrangement in the plane. Image data and additional information or meta information are thus combined without any relevant information loss in a single unit and in a manner such that they can be very simply accessed again. The meta information can be the identity of the camera that was the source of the view, the perspective of the camera, in particular also only in the form of a category such as at the top or right front, or a positional indication where a view is to be arranged in a net or in a three-dimensional reconstruction of the object. Non-exclusive examples for the format of a structured file are XMS (extensible markup language) or JSON (JavaScript object notation).

In a preferred further development, a reading tunnel for detecting optical codes on objects is provided that has a detection apparatus in accordance with the invention as well as a conveying device that conveys objects through the reading tunnel. The object moves past the sensors in the reading tunnel and is recorded in this movement. A reading tunnel can comprise a further sensor system, for example a scale or an RFID apparatus.

The method in accordance with the invention can be further developed in a similar manner and shows similar advantages in so doing. Such advantageous features are described in an exemplary, but not exclusive manner in the subordinate claims dependent on the independent claims.

BRIEF DESCRIPTION OF THE DRAWINGS

The invention will be explained in more detail in the following also with respect to further features and advantages by way of example with reference to embodiments and to the enclosed drawing. The Figures of the drawing show in.

DETAILED DESCRIPTION

Figure 1:
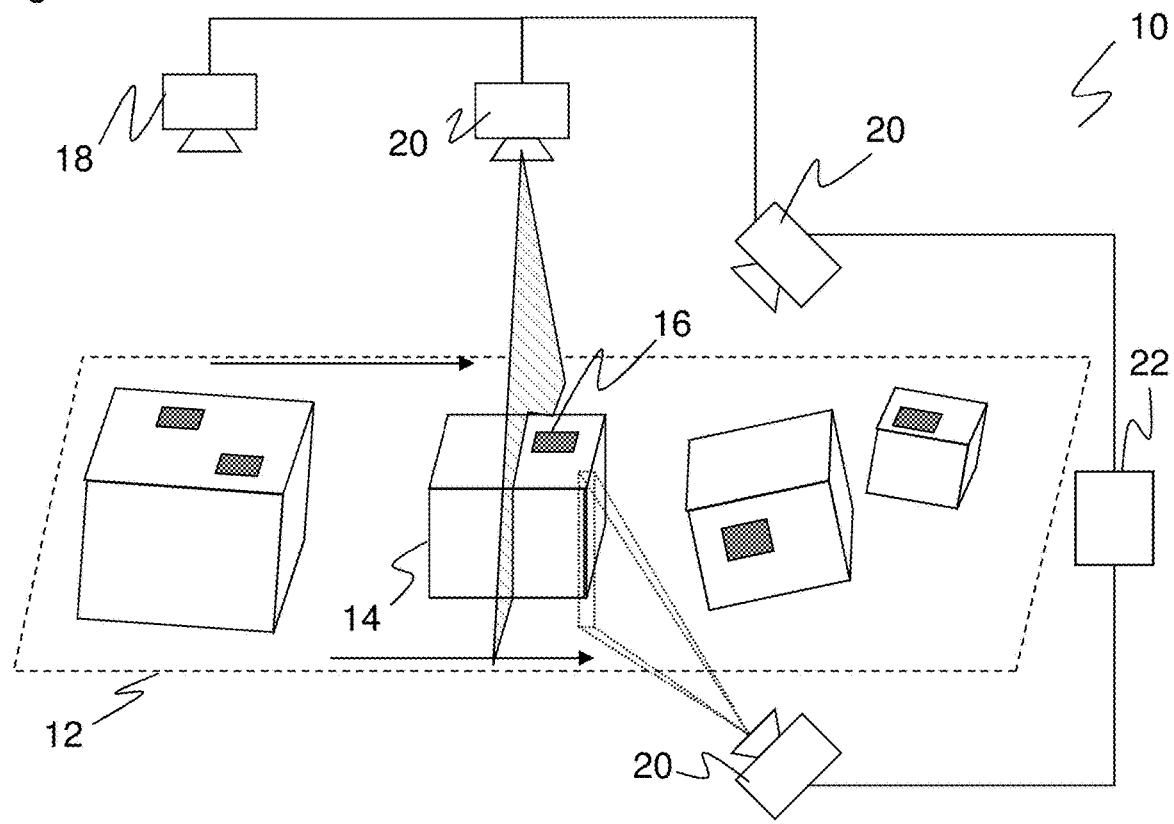
FIG. 1 a schematic three-dimensional representation of a reading tunnel with a detection apparatus composed of a plurality of optoelectronic sensors.

FIG. 1 shows in a three-dimensional schematic representation an embodiment of a detection apparatus 10 in accordance with the invention that is mounted above a conveying device 12 such as a conveyor belt on which objects 14 are moved in the direction indicated by arrows. The objects 14 bear code information 16, for example barcodes, two-dimensional codes or address labels. In an embodiment as a reading tunnel, it is the object of the detection apparatus 10 to detect the code information. In this respect, however, the object of the detection apparatus 10 can be limited to providing corresponding image data; the decoding can selectively take place in the detection apparatus 10 or downstream thereof. It is also conceivable that the objects 14 do not bear any code information 16 or that the detection apparatus 10 is not interested in the code information 16, but rather in the purely image information of the objects 14.

A geometry detection sensor 18 arranged upstream with respect to the conveying direction records the geometrical profile of the objects 14 moved passed it. The geometry detection sensor 18 can be configured as a laser scanner. No geometry detection sensor 18 is provided in other embodiments.

Cameras 20, here in the form of line cameras having linear CCD or CMOS image sensors that are mounted at different sides of the conveying device 12, record the actual image data to be detected In this respect, at least one of these cameras 20 can also take over the functionality of the geometry detection sensor 18. Three cameras 20 are shown in FIG. 1. However, different from the representation, more cameras are preferably provided to detect objects 14 from more sides or from all sides. Conversely, fewer cameras are also conceivable in principle.

An evaluation unit 22 that can also take over a control function is connected to the geometry detection sensor 18 and to the cameras 20. The evaluation unit 22 receives from the geometry detection sensor 18, if it is present, its geometry data and the image data of the respectively recorded line from the cameras 20. The image data read out linewise are successively composed to form one image in the course of the movement of the objects 14 on the conveying device 12. Alternatively, matrix sensors are used as cameras 20 instead of the line cameras, with then the success composition being able to be dispensed with or taking place in substantially larger steps with larger image zones. To correctly assemble the information detected at different positions in part, in particular the information of the geometry detection sensor 18 and of the cameras 20, a speed sensor is preferably provided, for example an incremental encoder, that determines the conveying speed of the conveying device 12.

Figure 2:
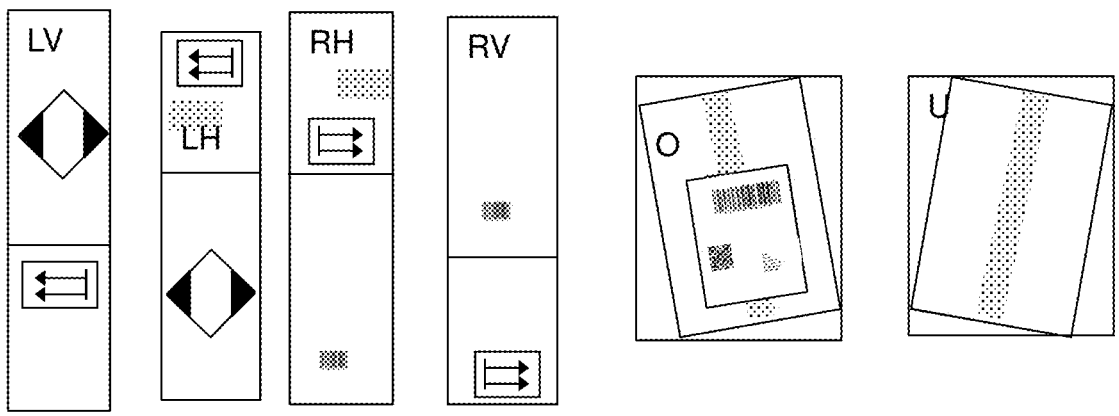
FIG. 2 a representation of exemplary shots of the sensors in their original form.

FIG. 2 shows exemplary images that are recorded by a detection apparatus having six cameras 20. The images are respectively marked by LV for a camera at the front left, by LH at the back left, by RH at the back right, RF at the front right, O from above and U from below. Individual cameras 20 can also be omitted, for example the camera with a perspective from below. Since the lateral cameras LV, LH, RH, RV have an oblique perspective, they as a rule detect two sides of an object 14, as can also be recognized in FIG. 2. This means that partly redundant image information is available in the further processing. This redundancy can be resolved in that the doubled image data are discarded. Alternatively, the doubled image data are offset with one another or at least the image data with the better quality are selected.

Conventionally, images as shown in FIG. 2 are output by the detection apparatus 10 and individually processed. In accordance with the invention, a combining processing takes place beforehand, in particular with a selection of suitable sections, of an adaptation and of a rearrangement that will be described in the following. The implementation of this processing can practically be distributed as desired over the cameras 20 and the evaluation unit 22. External systems such as a vision box or network-based processing units such as a server or a cloud can be involved in or take over this processing. It is conceivable that image data are packed and unpacked at times to restrict the required memory and the bandwidths of the transfer. Different conventional image processing such as filters, brightness adjustment, binarization and the like are also possible at practically all parts of the processing.

Figure 3:
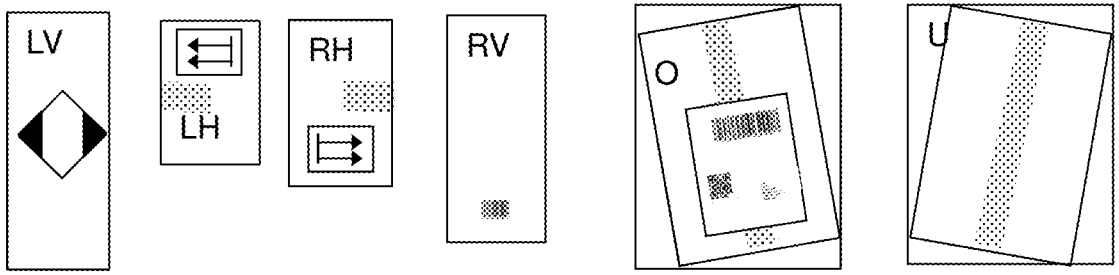
FIG. 3 a representation in accordance with FIG. 2 after the cutting out of a respective side of the detected object.

FIG. 3 shows the result of a processing in which views of a respective side of the recorded object 14 are selected from the images in accordance with FIG. 2. The relevant image section is selected for this purpose. In this respect, in particular the double shots of the lateral cameras 20 are eliminated. Only the necessary views remain, namely a view from each side, and these views are sufficient to record all the information on the object 14.

Figure 4:
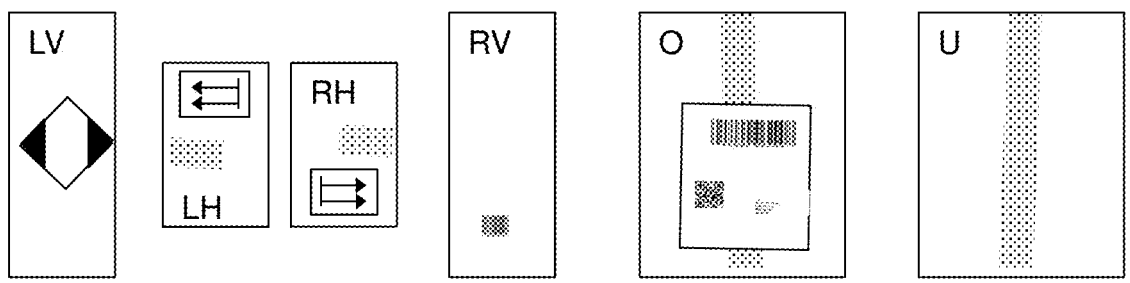
FIG. 4 a representation in accordance with FIG. 3 after a rotation and a rescaling that brings the views into a mutually comparable format.

FIG. 4 shows the result of a further processing in which the views in accordance with FIG. 3 are rotated and rescaled. This primarily relates to the views O, U from the top and bottom in the example. It is ensured by this step that the views have a defined orientation and additionally match one another in size and scale.

Figure 5:
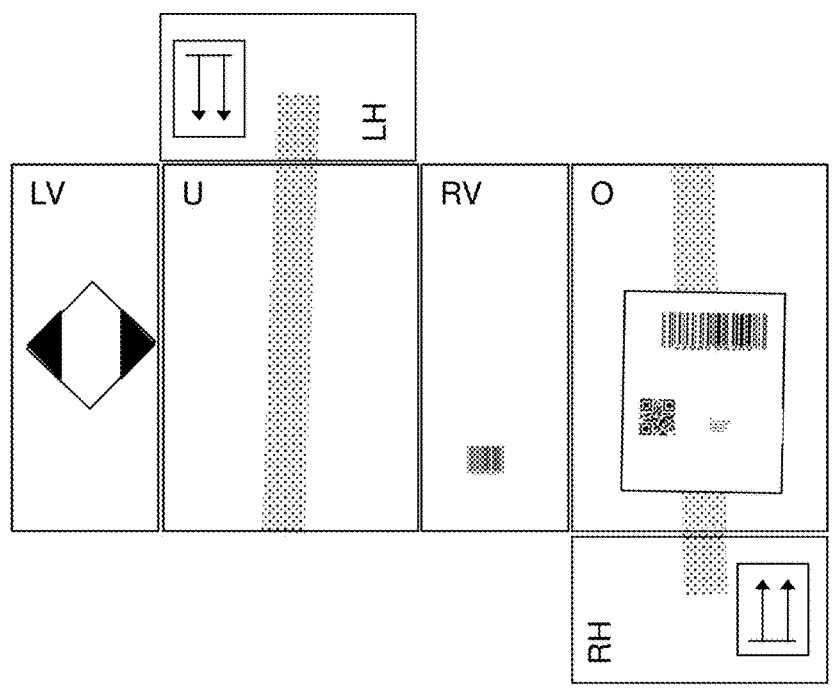
FIG. 5 a representation in accordance with FIG. 4 after a rearrangement of the views to form a net of the original object.

Finally, FIG. 5 shows the result of a rearrangement of the views in accordance with FIG. 4 that has the effect that a logical cohesion is produced. This is preferably a folding of the object 14, as shown in FIG. 5. The unambiguous association of the views to the sides of a cuboid can immediately be recognized. A downstream evaluation could directly restore the cuboid or could selectively show any desired side or could further evaluate its image information. The folded shape is also called a net geometrically. Similar arrangements are also conceivable for other forms than a cuboid. In addition, a net of a cuboid can be used if the actual shape of the object 14 differs, for instance shows specific curvatures or shear. The corresponding artifacts are at least tolerable up to a certain degree.

The rearranged views can be output as a common assembled image. Alternatively, the views remain separate images, but meta information is output with the views and the arrangement can be easily restored from this information, for example in that the associated camera 20 or perspective is indicated or in that coordinates and a direction of rotation with respect to the respective view are output that correspond to the position and orientation of the rearrangement, for example in accordance with FIG. 5. Such meta information on the individual views is preferably also output with a common image. In all these cases, the views are associated with the sides of the object via the image data and the meta information and it is unambiguously possible to access a view of a desired side or to separate the view.

The common image with the views or a plurality of images of views can be combined together with the meta information in a structured description or file. Examples for a suitable format are XML or JSON.

The invention claimed is:

1. A detection apparatus, the detection apparatus comprising:
    a plurality of optoelectronic sensors that are arranged in different positions and orientations to record respective image information of different sides of an object; and
    an evaluation unit to process the image information,
    wherein the evaluation unit is configured, in a combining processing operation, to select views of respective sides of the object in the image information of the plurality of optoelectronic sensors and to rearrange the views in a plane such that the original arrangement on the object can be restored.

2. The detection apparatus in accordance with claim 1, wherein the evaluation unit is configured to arrange the views in a net.

3. The detection apparatus in accordance with claim 2, wherein the evaluation unit is configured to arrange the views in the net of a cuboid.

4. The detection apparatus in accordance with claim 1, that has a geometry detection unit that is configured for the detection of the geometry of the objects with reference to at least one of distance data and a remission behavior of the objects.

5. The detection apparatus in accordance with claim 1, wherein the sensors are arranged for an omnidirectional reading from all sides.

6. The detection apparatus in accordance with claim 1, wherein the evaluation unit is configured to cut out a respective view from the image data.

7. The detection apparatus in accordance with claim 1, wherein the evaluation unit is configured to adapt the views to one another.

8. The detection apparatus in accordance with claim 7, wherein the evaluation unit is configured to adapt the views to one another by rotation and/or rescaling.

9. The detection apparatus in accordance with claim 1, wherein the evaluation unit is configured to combine the views in the arrangement in a plane to form one image.

10. The detection apparatus in accordance with claim 1, wherein the evaluation unit is configured to output views with information on their arrangement with respect to one another.

11. The detection apparatus in accordance with claim 1, wherein the evaluation unit is configured to output a structured description with views and information on at least one of its identity and arrangement in the plane.

12. The detection apparatus in accordance with claim 1, wherein the evaluation unit is configured to output a structured file with views and information on at least one of its identity and arrangement in the plane.

13. A reading tunnel for detecting optical codes on objects having a detection apparatus and having a conveying device that conveys objects through the reading tunnel, the detection apparatus comprising:
a plurality of optoelectronic sensors that are arranged in different positions and orientations to record respective image information of different sides of an object; and
an evaluation unit to process the image information,
wherein the evaluation unit is configured, in a combining processing operation, to select views of respective sides of the object in the image information of the plurality of optoelectronic sensors and to rearrange the views in a plane such that the original arrangement on the object can be restored.

14. A method of detecting objects in which a plurality of optoelectronic sensors record respective image information of different sides of an object in different positions and orientations and the image information is evaluated,
wherein, in a combining processing operation, views of respective sides of the object are selected in the image information of the plurality of optoelectronic sensors and the views are rearranged in a plane such that the original arrangement on the object can be restored.

* * * * *